(12) United States Patent
Zoval et al.

(10) Patent No.: US 6,965,433 B2
(45) Date of Patent: Nov. 15, 2005

(54) OPTICAL BIODISCS WITH REFLECTIVE LAYERS

(75) Inventors: Jim V. Zoval, Lake Forest, CA (US); Horacio Kido, Niland, CA (US); Jorma Antero Virtanen, Irvine, CA (US)

(73) Assignees: Nagaoka & Co., Ltd., Hygo (JP); Burstein Technologies, Inc., Irvine, CA (US)

( * ) Notice: Subject to any disclaimer, the term of this patent is extended or adjusted under 35 U.S.C. 154(b) by 0 days.

(21) Appl. No.: 09/999,274

(22) Filed: Nov. 15, 2001

(65) Prior Publication Data

US 2002/0163642 A1 Nov. 7, 2002

Related U.S. Application Data

(60) Provisional application No. 60/249,391, filed on Nov. 16, 2000, and provisional application No. 60/257,706, filed on Dec. 22, 2000.

(51) Int. Cl.[7] .......................... G01N 21/55; G01N 1/00; C12M 1/00
(52) U.S. Cl. ..................... 356/445; 356/246; 435/283.1
(58) Field of Search ................ 356/246, 436, 356/437, 440, 445; 435/6, 283.1, 287.1; 436/524

(56) References Cited

U.S. PATENT DOCUMENTS

| 5,462,839 A | 10/1995 | de Rooij et al. |
| 5,535,182 A | 7/1996 | Itoi |
| 5,550,063 A | 8/1996 | Bogart |
| 5,593,838 A | 1/1997 | Zanzucchi et al. |
| 5,605,662 A | 2/1997 | Heller et al. |
| 5,698,299 A | 12/1997 | Schmidt et al. |
| 5,737,478 A | 4/1998 | Yamagishi et al. |
| 5,843,767 A | 12/1998 | Beattie |
| 5,962,081 A | 1/1999 | Ohman et al. |
| 5,872,723 A | 2/1999 | DeCusatis et al. |
| 5,892,577 A * | 4/1999 | Gordon ....................... 356/73 |
| 5,949,745 A | 9/1999 | Kim |
| 5,953,513 A | 9/1999 | Saiki et al. |
| 5,959,280 A | 9/1999 | Kamatani |
| 6,007,889 A * | 12/1999 | Nee .......................... 428/64.1 |
| 6,026,068 A | 2/2000 | Obata et al. |
| 6,030,581 A * | 2/2000 | Virtanen .................... 422/68.1 |
| 6,042,684 A | 3/2000 | Ohman |
| 6,055,218 A | 4/2000 | Takeda et al. |
| 6,063,589 A * | 5/2000 | Kellogg et al. ................ 435/24 |
| 6,084,843 A | 7/2000 | Abe et al. |
| 6,088,507 A | 7/2000 | Yamauchi et al. |
| 6,103,399 A | 8/2000 | Smela et al. |
| 6,126,765 A | 10/2000 | Ohman |
| 6,140,135 A | 10/2000 | Landegren et al. |
| 6,147,941 A | 11/2000 | Kumagai |
| 6,147,943 A | 11/2000 | Ogasawara et al. |
| 6,154,427 A | 11/2000 | Yokota et al. |
| 6,160,953 A | 12/2000 | Fuchigami et al. |
| 6,451,402 B1 * | 9/2002 | Nee .......................... 428/64.1 |
| 6,734,401 B2 * | 5/2004 | Bedingham et al. ......... 219/388 |

FOREIGN PATENT DOCUMENTS

| CA | 2 361 700 | * | 8/2000 |
| DE | 199 38 839 A1 | * | 8/2000 |
| EP | 0 417 305 A1 | | 3/1991 |
| WO | WO 96/04547 | | 2/1996 |
| WO | WO 98/01533 | | 1/1998 |
| WO | WO 98/07019 | | 2/1998 |
| WO | WO 98/12559 | | 3/1998 |
| WO | WO 98/32535 | | 7/1998 |
| WO | WO 98/37238 | | 8/1998 |
| WO | WO 98/45693 | | 10/1998 |
| WO | WO 98/53311 | | 11/1998 |
| WO | WO 00/05582 | | 2/2000 |
| WO | WO 01/30500 A1 | | 5/2001 |
| WO | WO 01/54810 A1 | | 8/2001 |

* cited by examiner

*Primary Examiner*—Alan Mathews
(74) *Attorney, Agent, or Firm*—Knobbe Martens Olson & Bear LLP

(57) ABSTRACT

An optical biodisc has a substrate, a first reflective layer over the substrate, an opening in the first reflective layer for receiving an investigational feature, and a second reflective layer over the opening for reflecting light transmitted through the substrate.

6 Claims, 7 Drawing Sheets

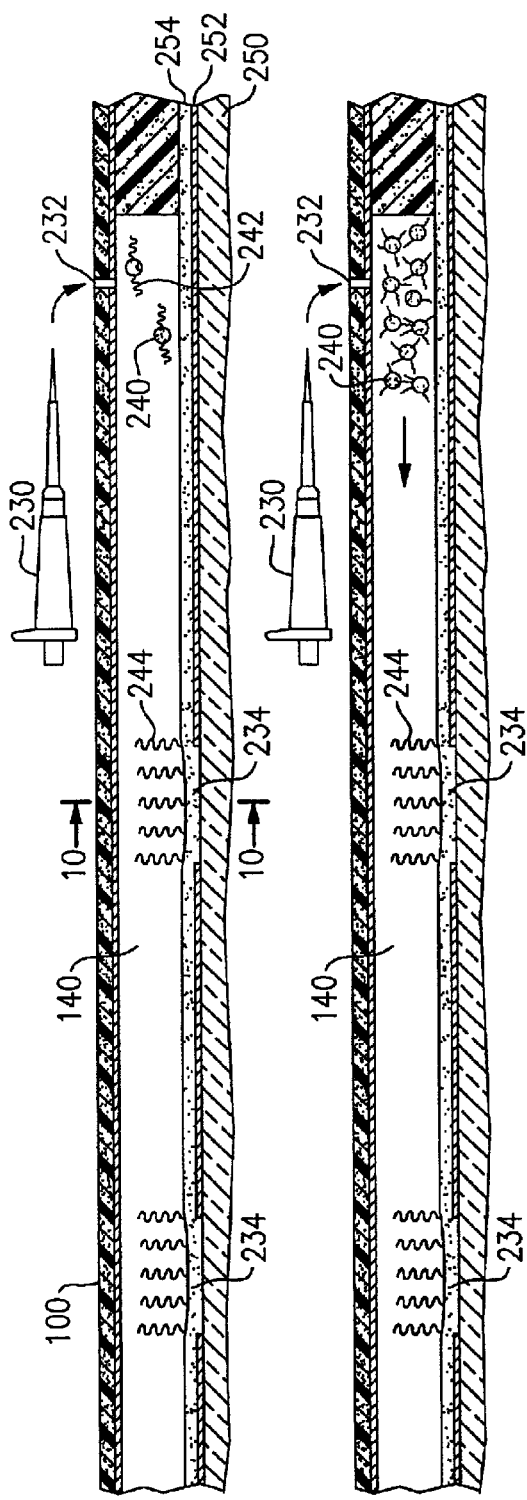
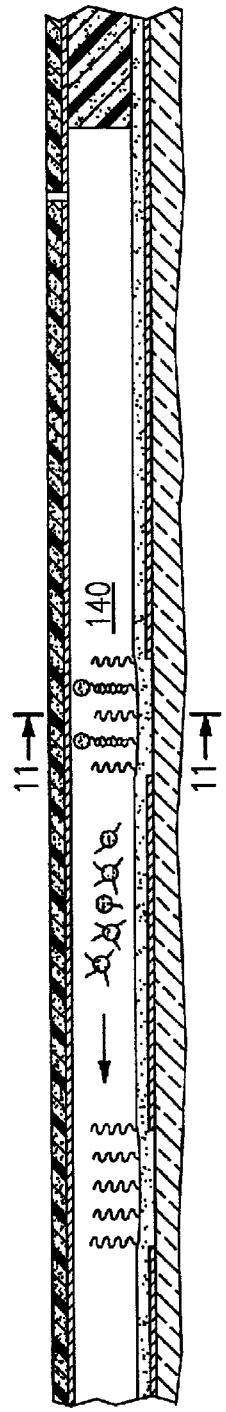
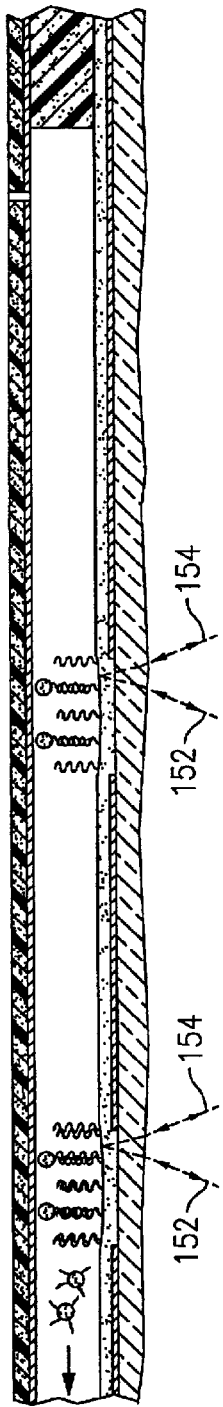
FIG.9A  FIG.9B  FIG.9C  FIG.9D

OPTICAL BIODISCS WITH REFLECTIVE LAYERS

CROSS REFERENCE TO RELATED APPLICATION

This application claims priority from U.S. Provisional Application Ser. No. 60/249,391, filed Nov. 16, 2000, and U.S. Provisional Application Ser. No. 60/257,705, filed Dec. 22, 2000, each of which is incorporated herein by reference.

BACKGROUND OF THE INVENTION

As shown in U.S. Pat. No. 6,030,581, an optical disc can be used to perform assays on biological or chemical samples. A sample can be provided in an opening and then moved by centrifugal force from one chamber or area to another chamber or area until it reaches an assay region where the sample (or a characteristic of the sample) can be observed.

As shown in U.S. Pat. No. 5,892,577, which also is incorporated herein by reference, a beam can be scanned over a rotating disc. Radiation reflected from and/or transmitted through the disc can be detected by a detector and used to read encoded information and/or detect assays.

SUMMARY OF THE INVENTION

The embodiments of the present invention allow reflected light to be used both to read operational data and to detect a biological or chemical investigational feature and/or a characteristic thereof. One embodiment includes a biodisc with a substrate, a reflective layer over the substrate for encoding information, an opening in the reflective layer at a viewing window where an investigational feature can be provided, and a second reflective layer spaced from the first reflective layer and at least over the viewing window such that light passing through the substrate to the viewing window can be reflected by the second reflective layer. The first reflective layer can be directly on the substrate or separated by intermediate layers, such as a dye layer. Over the second reflective layer, a cap portion can be provided.

The disc can have different configurations for channels and chambers for moving a sample, such as a generally U-shaped circuit or a series of chambers. At the viewing window, the investigational feature can be detected by one of a number of methods, including colorimetry, fluorimetry, the use of reporters, such as beads, or the use of other methods by which a sample, or a characteristic of a sample, can be observed. The disc can be used for medical diagnostics, such as detecting cholesterol or glucose levels, or for blood typing, detection of antigens, or any other desired biological or chemical interaction. The disc can also be used for imaging small objects.

A biodisc and drive system as described herein can have one or more of a number of different advantages, including an ability to detect investigational features with reflected light, to read encoded data in addition to investigational features, and the ability to use the focusing of a standard disc reader at the reflective layer where information is encoded. This means that with the disc shown in the embodiments, a conventional optical drive may be usable with few changes. Other features and advantages will become apparent from the following detailed description, drawings, and claims.

BRIEF DESCRIPTION OF THE DRAWINGS

FIGS. 9A–9D are cross-sectional views of an optical biodisc with investigational features being introduced and demonstrating a method according to an embodiment of the present invention.

DETAILED DESCRIPTION

Figure 1:
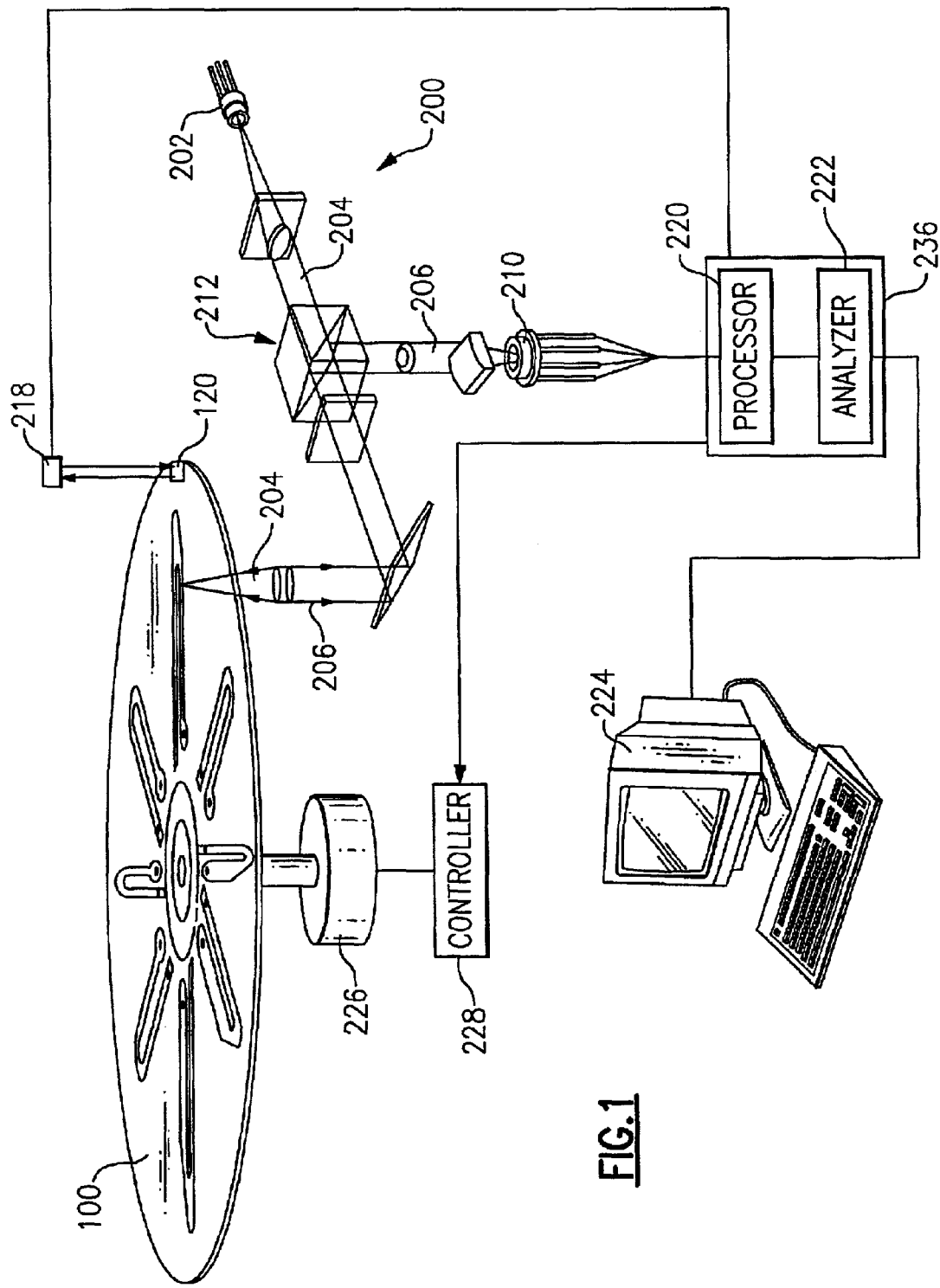
FIG. 1 is a perspective view of an optical biodisc and an associated reading system according to an embodiment of the present invention.

Optical biodiscs for assays according to the present invention may have any suitable shape, diameter, or thickness, but preferably are implemented on a round disc with a diameter, thickness, and materials similar to those of a compact disc (CD), a recordable CD (CD-R), a digital versatile disc (DVD), or one of a number of other formats. Compact discs, DVDs, and other such discs have encoded informational (operational) data, such as audio information or software. A biodisc according to embodiments of the present invention has investigational features, and preferably both encoded operational data and investigative features. The operational information can include data for performing, controlling, and post-processing a test or assay on a biological or chemical material. This operational information can include, for example, information for controlling the rotation rate of the disc, the direction of rotation of the disc, timing for rotation, stopping and starting of the disc, delay periods, multiple rotation steps, locations of samples, and control of the power of the light source.

Investigational features can include any chemical or biological material providing a test result. In one embodiment, target sequences, such as capture DNA strands or antibodies, are attached to a disc surface in a viewing window (also referred to as a viewing window). In the DNA example, a reporter is attached to a target DNA sequence, which is complementary to a capture DNA sequence. In the presence of a target sequence, the complementary capture DNA strand will hybridize with the target, thereby attaching DNA target sequences to the disc surface. In a subsequent wash step, unbound reporters are removed. A beam of light focused on the viewing window will determine the presence, or lack thereof, of a target sequence. Such a system is described in more detail in U.S. Provisional Application Ser. No. 60/257,705, filed Dec. 12, 2000, which is expressly incorporated by reference.

Other techniques for observing a sample or a characteristic of a sample include colorimetry and fluorimetry. In the case of colorimetry, a sample is provided in a viewing window, and the beam of light is directed to the sample. From the amount of light that is detected, information about the sample is derived.

An optical biodisc may generally be reflective, transmissive, and/or have some combination of reflective and transmissive portions. In the case of a reflective disc or in a reflective portion, an incident light beam may be focused onto a reflective surface of the disc, reflected by the reflective surface, and returned through optical elements to a detector as it would be in a conventional informational disc. In a transmissive disc or transmissive portion of a disc, light passes through the disc to a detector on the other side of the disc from the light source. The transmissive portions could be partially reflective. A transmissive disc is described in more detail in U.S. Provisional Application Ser. Nos. 60/255,233, filed Dec. 12, 2000; 60/294,051, filed May 29, 2001; 60/306,266, filed Jul. 18, 2001; 60/306,599, filed Jul. 19, 2001; and 60/291,233, filed May 16, 2001, each of which is incorporated herein by reference.

The embodiments of the present invention relate mainly to reflective biodiscs which provide both operational and investigative features, but the disc could include transmissive portions as well.

FIG. 1 shows an optical disc 100 and disc drive system 200. This disc drive system may be a conventional reader for CD, CD-R, DVD, or other known comparable format with modifications to software and minimal or no modifications to hardware, a modified version of a conventional disc drive, or a distinct dedicated disc drive device oriented to detecting investigational features. The basic components of such a disc drive system are a light system for providing light, a motor for rotating the disc, and a detection system for detecting light.

A light source 202 provides light to optical components 212 to produce an incident light beam 204, which may be collimated or non-collimated. In the case of a reflective portion of disc 100, incident light beam 204 is reflected off disc 100 to produce a return beam 206. Return beam 206 passes through optical components 212, and then to a detector 210. This detector can be a conventional optical disc drive detector or a modified detector.

Optical components 212 can include a lens, a beam splitter, and a quarter wave plate that changes the polarization of the light beam so that the beam splitter directs a reflected beam through the lens to focus the reflected beam onto the detector. These are conventional components in optical disc drives. An astigmatic element, such as a cylindrical lens, may be provided between the beam splitter and detector to introduce astigmatism in the reflected light beam.

Data from detector 210 is provided to a computer 236, including a processor 220 and an analyzer 222, and then to a monitor 224 to display an image or results. This computer 236 can represent a desktop computer, programmable logic, or some other processing device, and also can include a connection (such as over the Internet) to other processing and/or storage devices. A drive motor 226 and a controller 228, which can be connected to computer 236, are provided for controlling the rotation of disc 100. Thus if encoded operational data on disc 100 indicates that disc 100 is to be rotated at a certain rate, computer 236 can direct controller 228 to drive motor 226 at that rate. Computer 236 and controller 228 can be on the same computer.

The disc can have a physical mark referred to as a trigger mark 120. A hardware trigger sensor 218 is used to detect trigger mark 120. Trigger sensor 218 provides a signal to computer 236 that controls the collection and/or use of detected data by computer 236. In one embodiment, computer 236 only stores and analyzes data relating to investigational features when trigger sensor 218 detects trigger mark 120. In this case, data regarding investigational features is collected and analyzed when the trigger is detected. The trigger is preferably aligned radially with viewing windows. Trigger sensor 218 and trigger mark 120 can be located under disc 100 and on the bottom side of disc 100, respectively.

With a transmissive disc, there would also be a top detector on the other side of the disc from the light source. Transmissive disc detection is shown, for example, in U.S. Provisional Application Ser. Nos. 60/270,095, filed Feb. 20, 2001; 60/292,108, filed May 18, 2001; 60/292,110, filed May 18, 2001; 60/313,917, filed Aug. 21, 2001; and in Gordon, U.S. Pat. No. 5,892,577, filed Apr. 6, 1999, each of which is incorporated herein by reference.

Disc drive system 200 is thus employed to rotate disc 100, read and process any encoded operational information stored on the disc, and detect chemical, biological, or biochemical investigational features in an assay region of the disc. Optionally, in a system such as a CD-R, disc drive system 200 can be used to write information to disc 100 either before or after the material in the assay zone is analyzed by the read beam of the drive.

Figure 2:
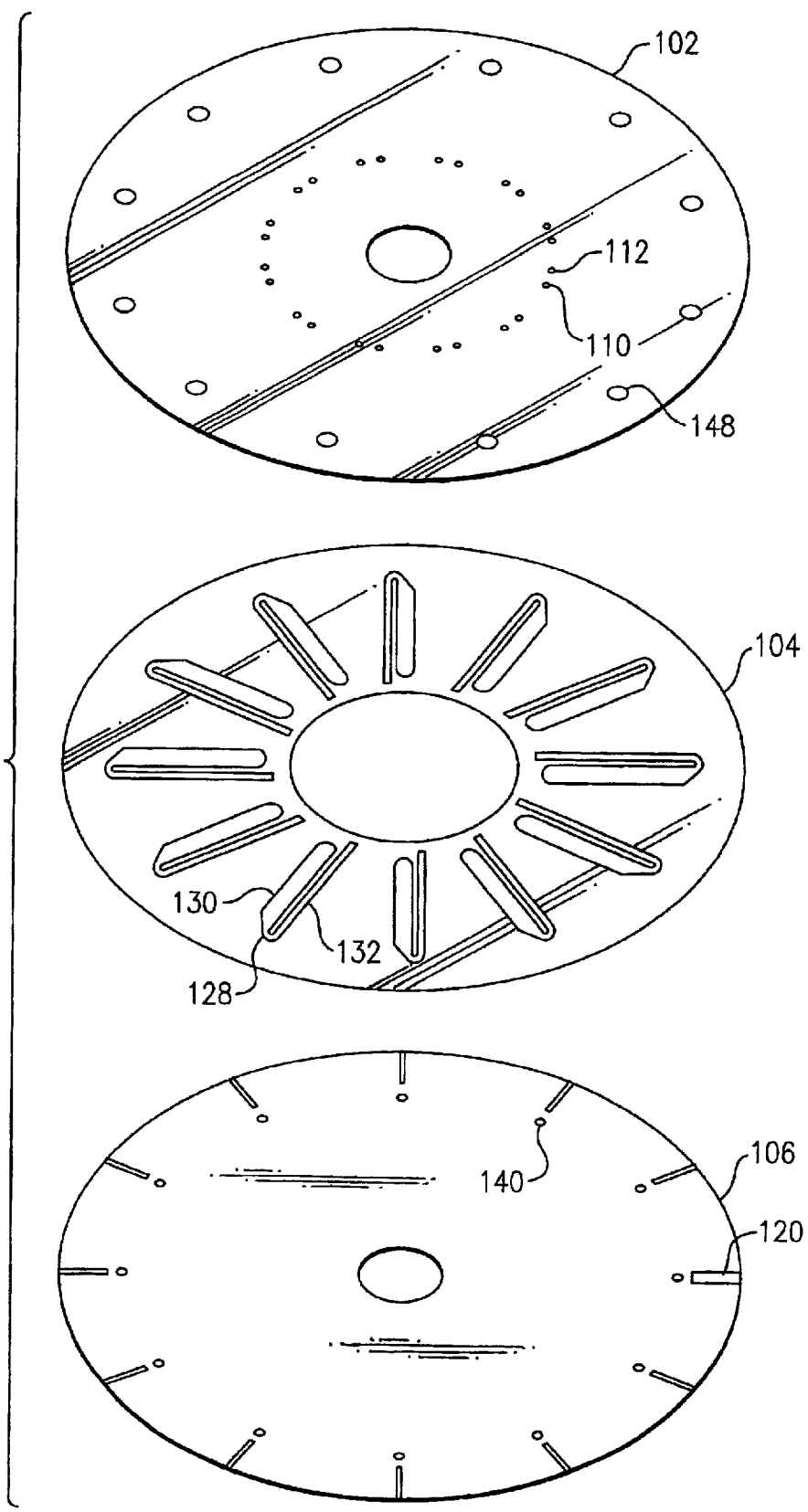
FIG. 2 is an exploded view of three structural layers of an optical biodisc according to embodiments of the present invention.

FIG. 2 shows three layers of an example of an embodiment of a reflective biodisc 100. The top layer, a cap 102, has inlet ports 110 for receiving samples, vent ports 112, and reflective layer regions 148, which are on the underside of cap 102. Cap 102 may be formed primarily from polycarbonate (e.g., about 1.2 mm thick). Reflective layer regions 148 are preferably made from a metal, such as aluminum or gold, with a sufficient thickness to be primarily or exclusively reflective.

A channel layer 104, also referred to as an adhesive layer, has fluidic circuits 128 formed therein preferably by stamping or cutting desired shapes from the layer. The channel layer can be over a capture layer where an investigational feature can bind. Each fluidic circuit 128 can have a flow channel 130 and a return channel 132. A fluidic circuit can include other microfluidic channels and chambers, such as preparatory regions and a waste region, as shown, for example, in the incorporated U.S. Pat. No. 6,030,581.

Substrate 106 is made up primarily of a layer of polycarbonate, and has a reflective layer deposited on the top of the polycarbonate layer. Viewing windows 140 are openings in the reflective layer that may be formed by removing portions of the reflective layer in any desired shape, or by masking viewing windows 140 before applying the reflective layer. One viewing window or a plurality of such windows can be oriented along one or more radii from the center of the disc. The reflective layer on substrate 106 is preferably formed from a metal, such as aluminum or gold, and can be configured with the rest of substrate 106 to encode operational information that is read with incident light.

In operation, samples are provided through inlet ports 110. When rotated, the sample moves outwardly from inlet ports 110 along a fluidic circuit 128. Through one of a number of biological or chemical reactions or processes, detectable investigational features may then be present in viewing windows 140.

The disc may be designed so that investigational features are captured to be in the focal plane coplanar with the reflective layer that has encoded information. This reflective layer is where an incident beam is typically focused conventionally through optical components and the optical properties of the substrate; alternatively, investigational features may be captured at a location in front of or at the focal plane, i.e., farther from the light source. The former configuration is referred to as a "proximal" type disc (see FIG. 4), and the latter a "distal" type disc (see FIG. 3).

Trigger marks 120 may be included on the surface of the reflective layer, and may include a clear window in all three layers of the biodisc, an opaque area, or a reflective or semi-reflective area encoded with information. The use of the trigger marks is described in conjunction with FIG. 1.

Substrate layer 106 may be impressed with a spiral track that starts at an innermost readable portion of the disc and then spirals out to an outermost readable portion of the disc. In a non-recordable disc such as a CD, this track is made up of a series of embossed pits with varying length, each typically having a depth of approximately one-quarter the wavelength of the light that is used to read the disc. The varying lengths and spacing between the pits encode the operational data. The spiral groove of a recordable CD-R disc has a detectable dye rather than pits.

Numerous designs and configurations of an optical pickup and associated electronics may be used in the context of the embodiments of the present invention. Further details and alternative designs for compact discs and readers are described in *Compact Disc Technology*, by Nakajima and Ogawa, IOS Press, Inc. (1992); *The Compact Disc Handbook, Digital Audio and Compact Disc Technology*, by Baert et al. (eds.), Books Britain (1995); and *CD-Rom Professional's CD-Recordable Handbook. The Complete Guide to Practical Desktop CD*, Starrett et al. (eds.), ISBN:0910965188 (1996); all of which are incorporated herein in their entirety by reference.

Figure 3:
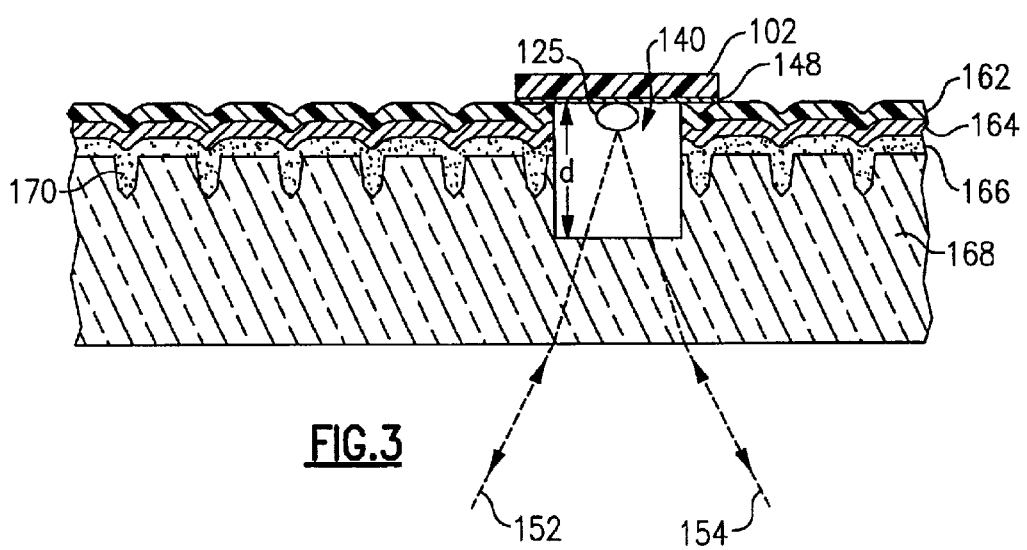
FIGS. 3–8 are cross-sectional views of a disc according to embodiments of the present invention.
Figure 4:
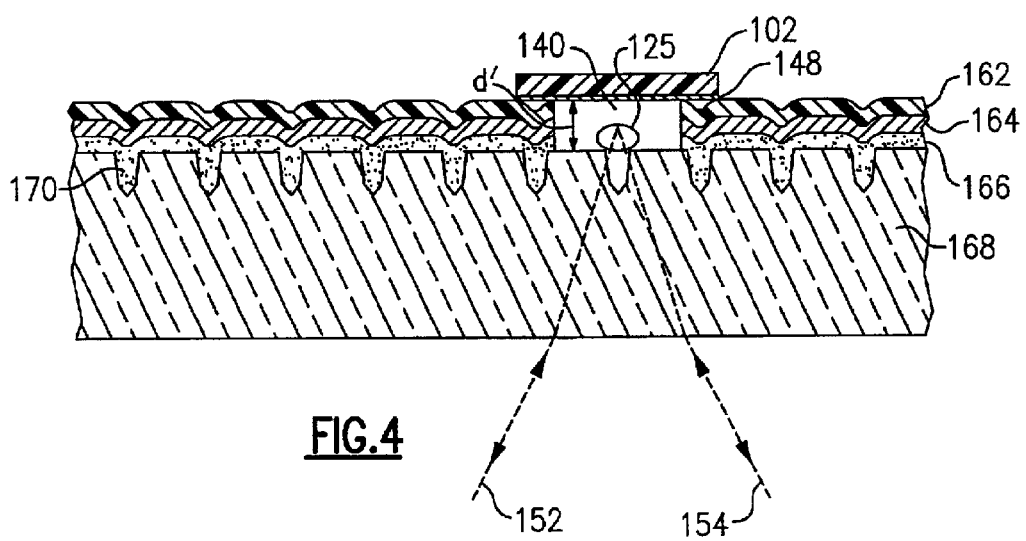

FIGS. 3 and 4 are cross-sectional views of an embodiment of a reflective biodisc, similar to a CD-R disc, shown with alternative depths for a viewing window 140 where an investigational feature 125 could be. Investigational feature 125 may be suspended with a capture layer at the top or bottom of the viewing window.

In FIG. 3, viewing window 140 is covered by a cap layer with lacquer 102 (e.g., about 0.5 microns) and a reflective layer 148, e.g., of gold or aluminum. Viewing window 140 is etched into a layer of lacquer 162, a reflective coating layer 164, a layer of dye 166, and a portion of substrate 168. In this embodiment, viewing window 140 has a depth d greater than the sum of the depths of layers 162, 164 and 166.

FIG. 4 is a cross-sectional view of a biodisc with a viewing window 140 of depth d' that is equal to the sum of the depth of the layers 162, 164, and 166 and does not cut into the layer of substrate 172. This configuration provides an investigational feature at the focal plane. Viewing window 140 is light transmissive and, other than the investigational feature, can have air, transmissive plastic, or a solution.

The layer of substrate 168 in FIGS. 3 and 4 includes a series of grooves 170. Grooves 170 are in the form of a spiral extending from near the center of the disc toward the outer edge and are implemented so that an interrogation beam may track along the spiral grooves 170 on the disc. This type of groove 170 is known as a "wobble groove." Grooves 170 are formed by a bottom portion having undulating or wavy side walls. A raised or elevated portion separates adjacent grooves 170 in the spiral. Dye layer 166 applied on the grooves 170 in this embodiment is, as illustrated, conformal in nature. At the viewing window in FIG. 4, layers 162, 164, and 166 are removed, as is dye 166 from grooves 170.

The path of an incident beam 152 is directed toward disc 100 from the light source. Incident beam 152 is focused on a point in a focal plane coplanar with reflective layer 148 and continues upwardly traversing through viewing window 140 to eventually fall incident onto reflective surface 148. At this point, incident beam 152 is reflected back and thereby forms a return beam 154. Without reflective layer 148 being added, the viewing window would be transmissive. This model applies for the behavior of the light beams for FIG. 4 through FIG. 8. The wavelength of the incident beam can be, for example, 540 nm, 640 nm, or 780 nm for different types of reading (and recording) formats.

Figure 5:
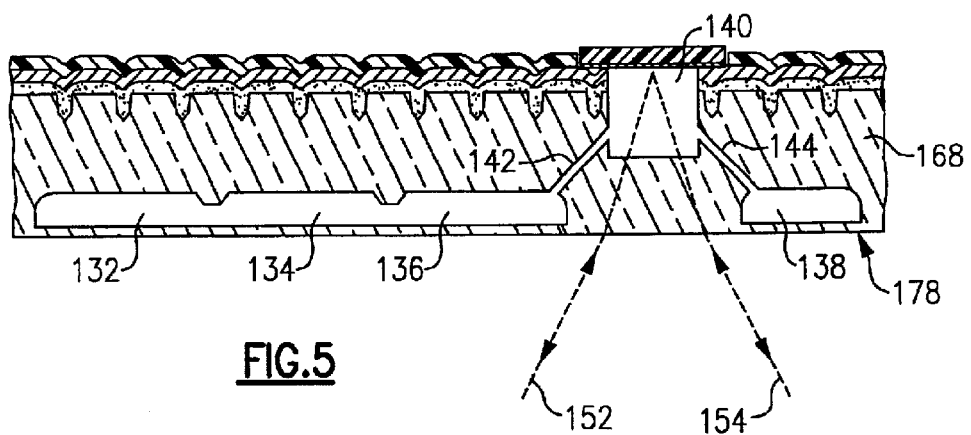
Figure 6:
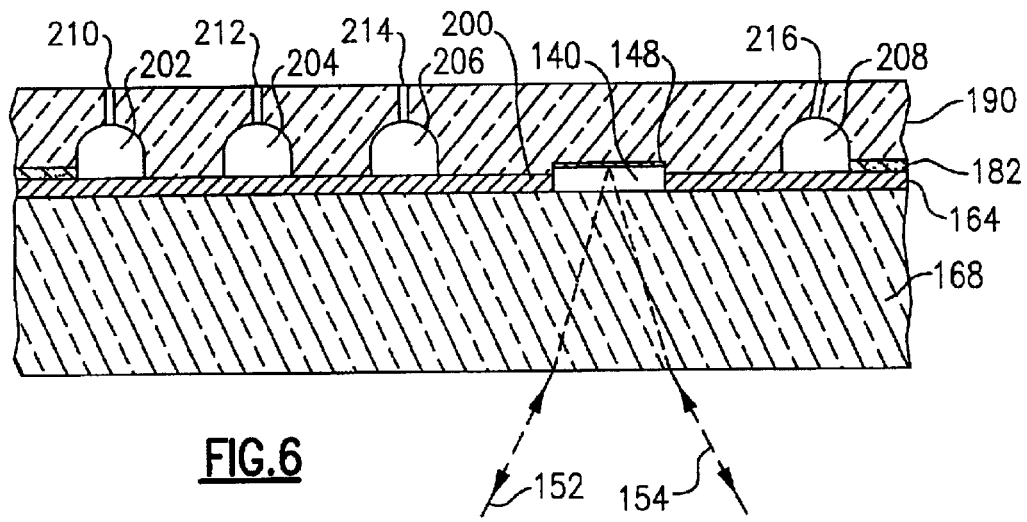
Figure 7:
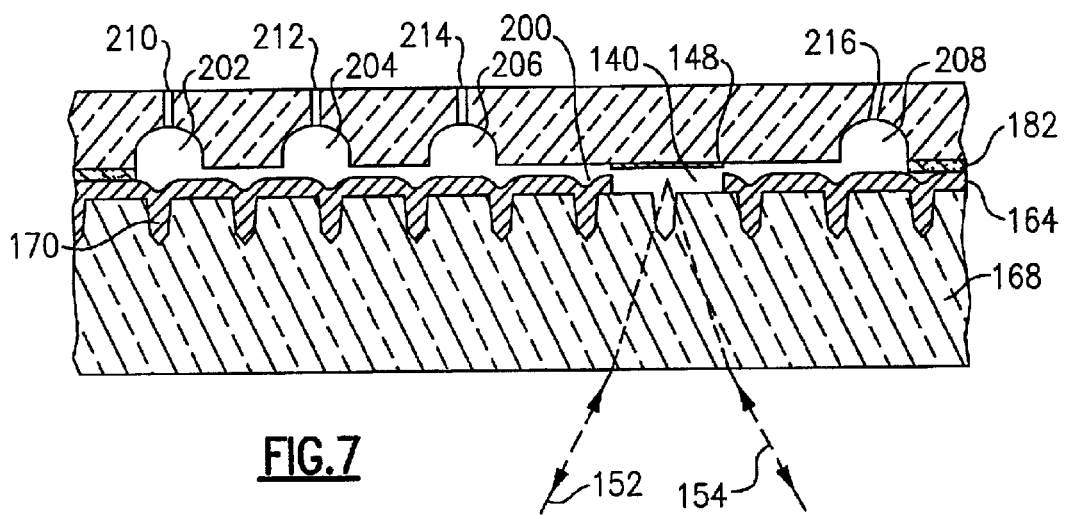

FIGS. 5, 6, and 7 are cross-sectional views of a biodisc with various embodiments of fluidic channels that have other chambers, such as input preparation and waste chambers as shown, for example, in the incorporated U.S. Pat. No. 6,030,581.

In FIG. 5, a fluidic channel 178 formed in substrate 168 has reservoirs 132, 134, and 136, and a waste chamber 138. Reservoirs 132, 134, and 136 are connected to viewing window 140 by capillary channel 142. Waste chamber 138 is also connected to viewing window 140 by vent 144. Viewing window 140, which is generally similar to that shown in FIG. 3, is covered by a cap layer of lacquer 102 and a reflective layer 148.

A sample can thus be provided to reservoir 132, provided through reservoirs 134 and 136 to capillary channel 142 to viewing window 140. The movement from reservoir 132 to viewing window 140 can be all at once, or in a series of stages governed by physical resistance and different speeds of rotation—in other words, rotation at a first rotation rate moves the sample from reservoir 132 to 134, rotation at a second rotation rate moves the sample from reservoir 134 to 136, and then rotation at a third rotation rate moves the sample from reservoir 136 to viewing window 140. Delays for heating, incubating, or some other purpose can be provided between steps.

FIGS. 6 and 7 show embodiments of a biodisc in which fluidic circuits are located primarily in cap 190 and above the substrate 168 and reflective layer 164. In FIG. 6, chambers 202, 204 and 206 are input reservoirs with vents 210, 212, and 214. Waste chamber 208 has a vent 216. In this embodiment, the biodisc does not have a layer of lacquer 162 over reflective layer 164. Instead, a layer of adhesive 182 covers reflective layer 164.

Viewing window 140 is created by removing a portion of reflective layer 164. A reflective layer 148 is at the top of viewing window 140. FIG. 6 does not show a dye layer, and thus could represent, for example, a CD rather than CD-R.

FIG. 7 shows a cross-sectional view of an embodiment similar to that of FIG. 6, with grooves 170 etched into substrate 168. Reflective layer 164 is applied on substrate 168. Unlike some other embodiments in which dye is provided in grooves 170, the grooves 170 in this embodiment have the reflective layer material, such as gold or aluminum or any other suitable reflective material. Without a dye layer or an appropriate substitute, however, the drive cannot write data back to the disc.

Figure 8:
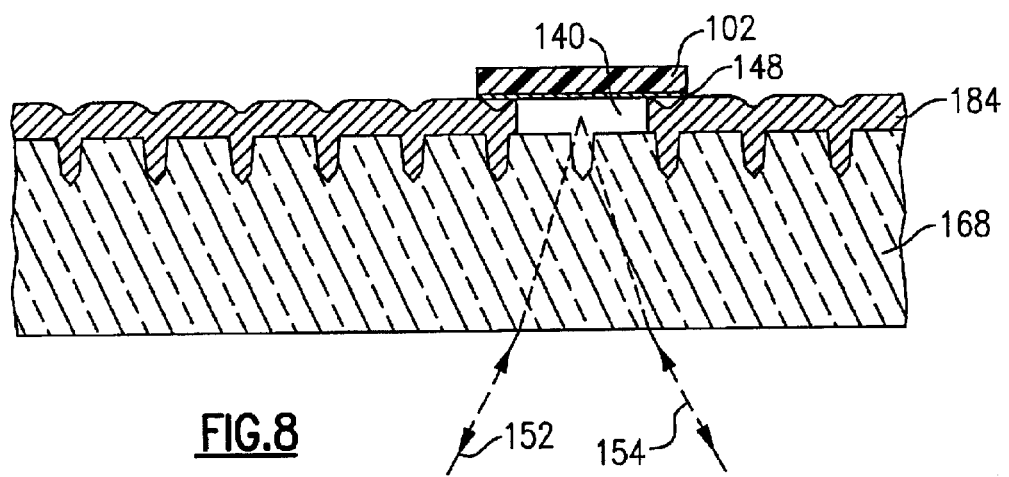

FIG. 8 is a cross-sectional view of a biodisc with only a reflective layer 184. Substrate 168 of the biodisc has tracking grooves 170 and a layer of conforming reflective material 184 on top. This embodiment does not include a lacquer layer 162 and a dye layer 166. Viewing window 140, which is created by removing a portion of reflective layer 164, is covered by a cap 102 of lacquer and a reflective layer 148.

FIGS. 9A–9D illustrate a method for detecting or determining the presence of target DNA in a sample in conjunction with an optical biodisc of the type described herein. In FIG. 9A, a pipette 230 is loaded with a test sample that has reporters 240 with target DNA 242. The disc has a substrate 250 and a reflective layer 252 over substrate 250. Reflective layer 252 is selectively removed (or selectively deposited initially) to have gaps where there are viewing windows 234. A capture layer 254 is over the substrate in the viewing windows 234, and may be over the entire reflective layer 252 as well. Capture DNA strands 244 are anchored to the capture layer in windows 234.

The test sample is injected or deposited into flow channel 140 through an inlet port 232. As flow channel 140 is further filled with test sample, reporters 240 with DNA sequences 242 flow in flow channel 140 as illustrated in FIG. 9B. When target DNA 242 of a specific sequence is present in the test sample, target DNA 242 hybridizes with the capture DNA 244, as shown in FIGS. 9C. and 9D.

In this manner, reporters 240 are retained within the viewing windows 234. Hybridization may be further facilitated by rotating disc 100 so that reporters 240 slowly move or tumble down flow channel 140. Slow movement allows ample time for additional hybridization. After hybridization, the disc may be rotated further to clear the viewing windows 234 of unattached reporters 240.

Interrogation beam 152 may then be scanned through viewing windows 234 to determine the presence of reporters 240 as illustrated in FIG. 9D. In the event no target DNA 242 is present, all the reporters 240 are spun down flow channel 140 when disc 100 is rotated. In this case, when interrogation beam 152 is directed into viewing windows 234, a negative reading will thereby result indicating that no target DNA 242 was present in the sample.

Figure 10:
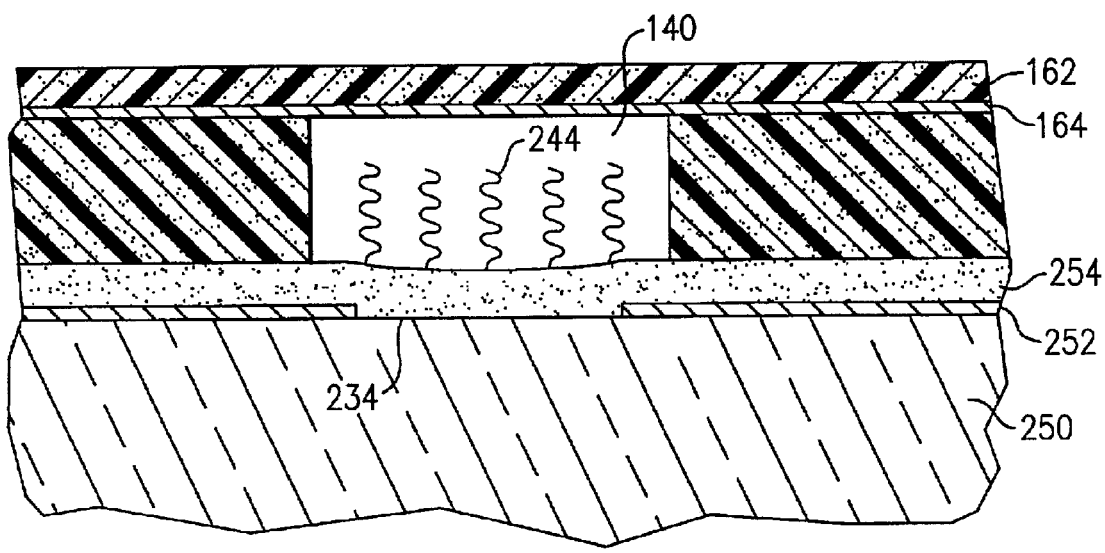
FIGS. 10 and 11 are cross-sectional views of FIGS. 9A and 9C, respectively.
Figure 11:
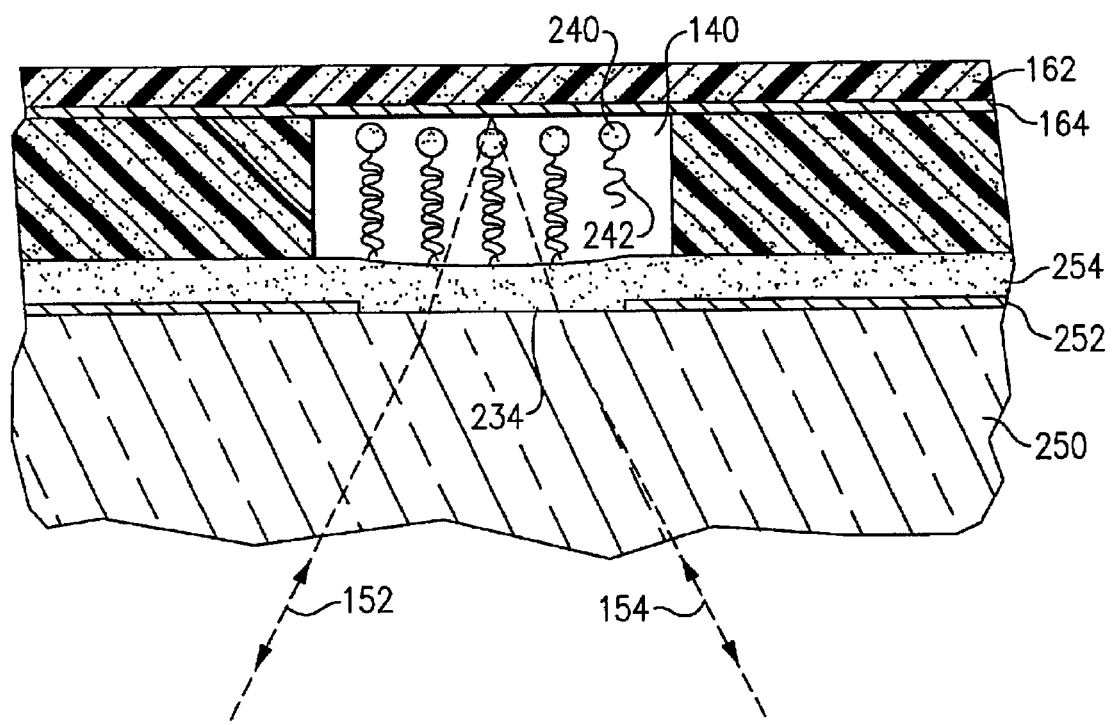

FIGS. 10 and 11 are cross-sectional views of FIGS. 9A and 9C, respectively. In FIG. 9A, capture DNA 244 is attached to the capture layer 254 within target window 234. When complementary target DNA 242 and reporter 240 are injected into viewing window 140, target DNA 242 and capture DNA 244 hybridize. Interrogation beam 152 then detects for reporters 240 after unattached reporters have been washed away.

Figure 12:
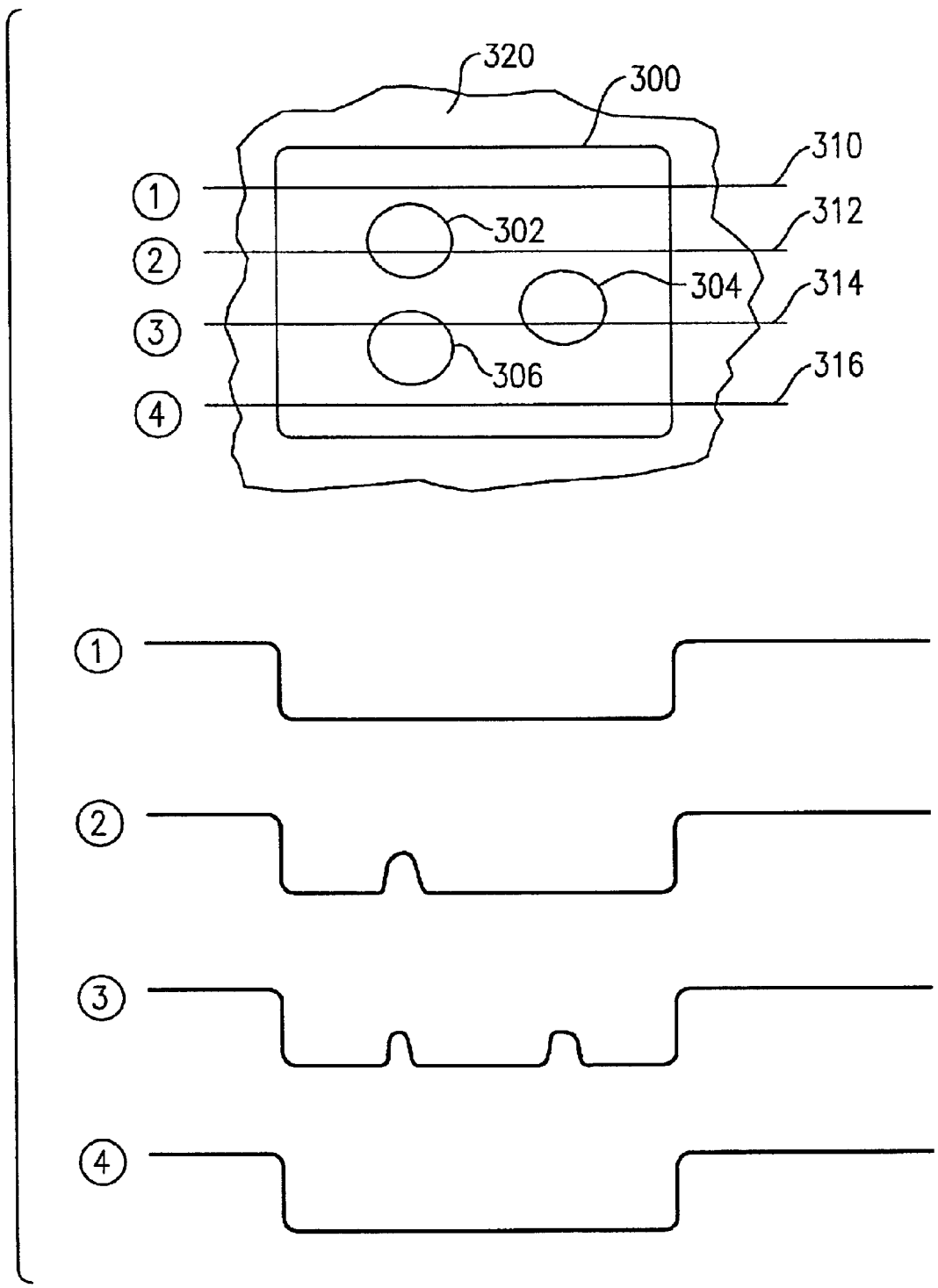
FIG. 12 is a graphical representation of detection signals of reporters according to an embodiment of the present invention.

FIG. 12 shows graphically a method for detecting reporters. In FIG. 12, a viewing window is shown with reporters 302, 304, and 306. These reporters could be beads, in the case where the binding is for DNA, or cells, in the case where the detection is of antigens on cells. The viewing window is shown with four tracks 310, 312, 314, and 316 of the disc. There could be many more tracks, and the tracks that are shown may actually be spaced apart with other track between them; e.g., the tracks shown here could be every fourth track. The spacing is preferably selected based on the size of the reporter being detected, such that the spacing between tracks that are read is about the size of a reporter so as to detect each reporter once. Around the viewing window is a reflective layer 320, which may include encoded operational information.

As the light beam moves along the tracks, the amount of reflected light is high outside of the viewing window. Within the viewing window, where the reflective layer under the cap is spaced from the focal point, the amount of reflected light declines. Within the viewing window, more light is reflected when the light beam reflects off the reporter. The analysis software thus looks for a drop-off and then increase in the amount of reflected light to detect the bounds of the viewing window. Within the viewing window, the analysis software looks for peaks that exceed a threshold and counts these peaks. The light then moves to the next track to be used, which may be several tracks away from the previously read track. Such a reading system is shown, for example, in U.S. Provisional Application Ser. No. 60/270,095, filed Feb. 20, 2001, which is expressly incorporated herein by reference.

Other detection methods may be used. The counting can be performed in hardware with edge detection circuitry. Other hardware and software methods can be used, including imaging and using image recognition software to detect individual reporters. Other detection methods may be more oriented to a yes/no decision. The boundary of the window can be determined from encoded information in the reflective layer near the window.

Having described several embodiments of the present invention, it should be apparent that modifications can be made without departing from the scope of the invention as defined by the appended claims. For example, the testing can be used for medical diagnostics, biological agent detection (including biological warfare), environmental testing, and forensic DNA analysis. A CD-type system can image microstructures, detect and count cells, detect microbeads (e.g., 1–6 microns) used in DNA and immuno-assays, detect colorimetric substrates used in enzymatic assays, and detect new or reported nanogold and nanocarbon. Assay techniques include Ab-Ag reaction, hybridization, enzyme cascade, chelation, binding to surface markers, and imaging by cell identification and agglutination. The references to physical relationship, such as one layer being "over" another, or light being provided to the "bottom" of the disc, are meant as terms of reference, but are not meant to literally be "over" necessarily; rather, the light could be directed from above with the structure upside down, or the disc could be on its side.

What is claimed is:

1. A method for forming an optical disc, comprising:

forming a first reflective layer over a substrate such that there is at least a first portion without the first reflective layer;

forming a second reflective layer on a second portion of a cap; and assembling the substrate and cap so that the substrate and cap are parallel along a first direction and the first portion and second portion are aligned along a second direction perpendicular to the first direction such that the second portion of the cap covers the first portion without the first reflective layer.

2. The method of claim 1, wherein the first reflective layer is formed over the substrate and a portion is removed.

3. The method of claim 1, wherein the first reflective layer is patterned over the substrate so that it is provided on the substrate with the first portion lacking.

4. The method of claim 1, further comprising forming a capture layer over the first portion, the capture layer adapted to receive a biological material for capturing a reporter introduced into a volume between the first and second portions.

5. The method of claim 1, further comprising providing a channel layer between the substrate and cap, the channel layer having a pattern cut out, such that when the substrate, cap, and channel layer are assembled, the pattern in the channel layer defines a fluidic channel in the optical disc.

6. The method of claim 5, further comprising forming an opening in the cap over a portion of the fluidic channel.

* * * * *